US00PP22075P2

(12) United States Plant Patent
Klemm et al.

(10) Patent No.: US PP22,075 P2
(45) Date of Patent: Aug. 9, 2011

(54) ***OSTEOSPERMUM* PLANT NAMED 'KLEOE09173'**

(50) Latin Name: ***Osteospermum ecklonis* Norl.**
Varietal Denomination: KLEOE09173

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,139

(22) Filed: Mar. 30, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt

(74) *Attorney, Agent, or Firm* — Jondle & Associates, P.C.

(57) ABSTRACT

An *Osteospermum* variety named 'KLEOE09173' particularly distinguished by a dark, purple-red flower color, very tolerant to various weather conditions, continuous flowering throughout the Summer, and a large flower size, is disclosed.

1 Drawing Sheet

Genus and species: *Osteospermum ecklonis* Norl.
Variety denomination: 'KLEOE09173'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE09173'. The new variety was discovered as a seedling resulting from a cross conducted in August 2006 in Stuttgart, Germany. The female parent was a proprietary *Osteospermum* plant named 'Astra Pink Yellow' (unpatented), and the male parent was a proprietary *Osteospermum* plant named 'Zion Red Zebra' (unpatented). A single plant selection was subsequently chosen for further evaluation and for asexual propagation.

The new variety was first propagated via vegetative cuttings in May 2007 in Stuttgart, Germany and has been asexually reproduced repeatedly by vegetative cuttings in Stuttgart, Germany for approximately 10 generations. The present invention has been found to retain its distinctive characteristics through successive asexual propagations via vegetative cuttings.

Plant Breeder's Rights for this variety have not been applied for. 'KLEOE09173' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Dark, purple-red flower color;
2. Very tolerant to various weather conditions;
3. Continuous flowering throughout the Summer; and
4. Large flower size.

DESCRIPTION OF THE PHOTOGRAPH

This new *Osteospermum* plant is illustrated by the accompanying photograph which shows a close-up of the flower of the plant. The colors shown are as true as can be reasonably obtained by conventional photographic procedures. The photograph was taken in Summer 2009 of a 7-month-old plant in the field in Stuttgart, Germany, under conditions which approximate those generally used in commercial practice.

DESCRIPTION OF THE NEW VARIETY

The following detailed descriptions set forth the distinctive characteristics of 'KLEOE09173'. The data which define these characteristics were collected from asexual reproductions carried out in Stuttgart, Germany. The plant history was taken in Summer 2009 on 7-month-old plants which were potted at 4 weeks in 12 centimeter containers and then planted in the ground in calendar week 20. The plants were pinched once at 6 weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Asteraceae.
- *Botanical name.*—*Osteospermum ecklonis* Norl.
- *Common name.*—African daisy.

Parentage:
- *Female parent.*—A proprietary *Osteospermum* plant named 'Astra Pink Yellow' (unpatented).
- *Male parent.*—A proprietary *Osteospermum* plant named 'Zion Red Zebra' (unpatented).

Plant:
- *Form and habit.*—Semi-upright (V-shape).
- *Growth habit.*—Medium vigorous.
- *Branching habit.*—Sparsely branching.
- *Height (from top of soil, including inflorescence).*—55.0 cm.
- *Width (including inflorescences).*—50.0 cm.
- *Propagation.*—Vegetative cuttings.

*Time to produce a finished flowering plant.*—18 weeks from sticking.
*Time to initiate and develop roots.*—4 weeks.
*Root description.*—Freely rooting.

Leaves:
*Arrangement.*—Alternate.
*Shape.*—Obovate.
*Apex.*—Acute.
*Base.*—Acute.
*Margin.*—Serrate.
*Color.*—Immature leaf: Upper surface: RHS N137D. Lower surface: RHS 137B. Mature leaf: Upper surface: RHS 137A. Lower surface: RHS 137B.
*Length.*—6.0 cm to 6.5 cm.
*Width.*—2.5 cm to 3.0 cm.
*Texture.*—Glabrous on the supper surface.
*Appearance.*—Leathery on the upper surface.
*Petioles.*—Absent.
*Venation pattern.*—No venation.

Stems:
*Total number of branches* (*calculated at the base of the plant*).—3 to 4.
*Length.*—50.0 cm to 55.0 cm.
*Diameter.*—1.0 cm.
*Internode length.*—0.7 cm to 1.2 cm.
*Color.*—RHS 144D and RHS N92A.
*Texture.*—Glabrous.
*Appearance.*—Leathery.
*Anthocyanin.*—Absent.

Inflorescence buds:
*Shape.*—Obovate.
*Length.*—1.5 cm to 1.8 cm.
*Diameter.*—1.2 cm.
*Color* (*at tight bud just before the ray florets unfold*).—RHS 141C.

Inflorescence:
*Type.*—Composite, single.
*Blooming habit.*—Plants flower continuously from Spring to Fall.
*Quantity of inflorescences per plant.*—Approximately 200.
*Lastingness of the inflorescences on the plant.*—10 days.
*Fragrance.*—Absent.
*Inflorescence diameter.*—3.5 cm to 6.0 cm.
*Inflorescence depth.*—Approximately 1.5 cm.
*Disc diameter.*—1.0 cm.

Disc floret:
*Quantity per inflorescence.*—Approximately 70.
*Shape.*—Tubular, radially symmetrical.
*Tube color.*—Closed: RHS N79A and RHS 199A. Mature: RHS N79A and RHS 199A.
*Length.*—Approximately 0.8 cm.
*Diameter* (*at apex*).—0.2 cm to 0.3 cm.
*Apex.*—Acuminate.
*Apex color.*—RHS N79A.
*Base.*—Obtuse.
*Base color.*—RHS 2D.
*Margin.*—Entire.

Ray floret:
*Quantity per inflorescence:* 20.
*Shape.*—Obovate.
*Color.*—Upper surface: RHS N79B and RHS N79D and RHS 167B. Lower surface: RHS N92A and RHS 83A and RHS 162B.
*Length.*—Approximately 3.0 cm.
*Width.*—0.8 cm.
*Apex.*—Obtuse.
*Base.*—Acute.
*Margin.*—Entire.
*Texture.*—Velvety.
*Peduncle.*—Length: 8.0 cm to 9.0 cm. Diameter: 0.2 cm. Texture: Rough. Color: RHS 143A.

Phyllaries:
*Arrangement.*—Single.
*Observed quantity per plant.*—Approximately 20.
*Shape.*—Lanceolate.
*Color.*—Upper surface: RHS 144A. Lower surface: RHS 143B (shiny).
*Length.*—0.9 cm to 1.1 cm.
*Width.*—0.15 cm to 0.25 cm.
*Apex.*—Acute.
*Base.*—Obtuse.
*Margin.*—Entire.
*Texture.*—Rough.

Reproductive organs:
*Androecium.*—Location: In the disc floret. Stamens: Quantity: Approximately 70. Shape: Tubular. Color: RHS N77A and RHS 2D at the base. Filament length: 0.2 cm. Filament diameter: 0.02 cm. Anther: Shape: Longitudinal. Color: RHS 202A. Length: 0.2 cm. Diameter: 0.02 cm. Pollen: Color: RHS 162A. Amount: Moderate.
*Gynoecium.*—Location: On the base of the petals (ray floret); pistils in the disc floret are degenerated and not functional. Pistils: Number: 20. Length: 0.4 cm to 0.6 cm. Diameter: 0.02 cm. Stigma: Color: RHS 202A. Shape: Ovate. Length: 0.2 cm. Diameter: 0.001 cm. Style: Color: RHS 186A. Length: 0.5 cm. Diameter: 0.001 cm.

Fruit and seed set: Double, brown, torpedo-shaped seeds; moderate seed set observed.

Disease and insect resistance: No particular disease or insect resistance observed.

COMPARISON WITH PARENTAL AND COMMERCIAL VARIETIES

'KLEOE09173' differs from the female parent, the proprietary *Osteospermum* plant named 'Astra Pink Yellow' (unpatented) in that 'KLEOE09173' has a medium, vigorous growth habit and dark, purple-red flowers, whereas 'Astra Pink Yellow' has a very compact growth habit and yellow-violet flowers.

'KLEOE09173' differs from the male parent, the proprietary *Osteospermum* plant named 'Zion Red Zebra' (unpatented) in that 'KLEOE09173' has upper petals that have a dark, purple-red color, and 'Zion Red Zebra' has upper petals that have a purple, pink, and white color.

'KLEOE09173' differs from the commercial variety 'KLE004113' (unpatented) in that 'KLEOE09173' has a medium, vigorous growth habit and dark, purple-red colored flowers, whereas 'KLE004113' has a compact growth habit and light, purple-red colored flowers.

We claim:

1. A new and distinct variety of *Osteospermum* plant named 'KLEOE09173' as shown and described herein.

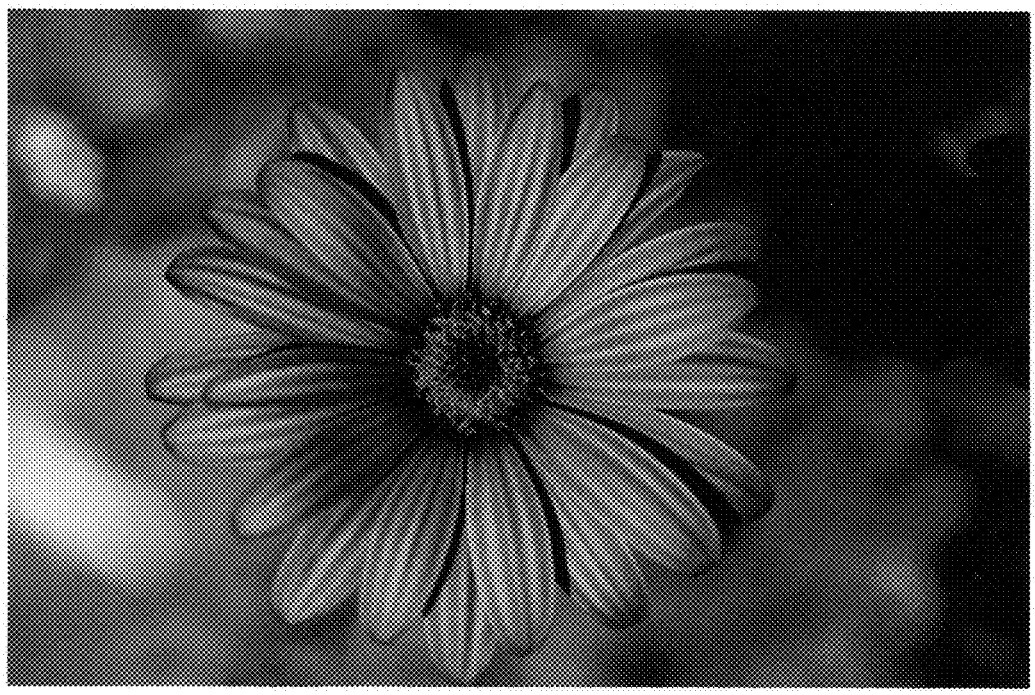

* * * * *